United States Patent [19]

Einarson et al.

[11] Patent Number: 4,806,014
[45] Date of Patent: Feb. 21, 1989

[54] METHOD FOR MEASURING SIZE DISTRIBUTION

[75] Inventors: Jens C. Einarson, Stockholm; Sven-Olof Lundqvist, Hägersten, both of Sweden

[73] Assignee: Svenska Traforskningsinstitutet, Stockholm, Sweden

[21] Appl. No.: 110,582

[22] Filed: Oct. 19, 1987

Related U.S. Application Data

[63] Continuation of Ser. No. 822,415, filed as PCT SE85/00118 on Mar. 14, 1985, published as WO85/04249 Sep. 26, 1985, abandoned.

[30] Foreign Application Priority Data

Mar. 14, 1984 [SE] Sweden .............................. 8401410

[51] Int. Cl.$^4$ ..................... G01N 15/02; G01N 21/85
[52] U.S. Cl. ...................... 356/335; 356/379
[58] Field of Search ..................... 356/335, 379, 380

[56] References Cited

U.S. PATENT DOCUMENTS

| | | | |
|---|---|---|---|
| 939,830 | 11/1909 | Haenke et al. | 193/32 |
| 3,409,187 | 11/1968 | Socha | 193/32 |
| 4,288,162 | 9/1981 | Sakamoto et al. | 356/335 |
| 4,514,816 | 4/1985 | Ollus et al. | 364/555 |

*Primary Examiner*—Richard A. Rosenberger
*Attorney, Agent, or Firm*—Burns, Doane, Swecker & Mathis

[57] ABSTRACT

The size distribution of wood chips for the manufacture of cellulose pulp is determined by an optoelectric measuring method and device. Light reflected from a conveying surface (2) and lump material distributed thereon, is recorded optically (3) at short time intervals, and recorded signals are processed electronically for obtaining the size distribution of the material over a number of selected size classes.

1 Claim, 3 Drawing Sheets

METHOD FOR MEASURING SIZE DISTRIBUTION

This application is a continuation of application Ser. No. 822,415, filed as PCT SE85/00118 on Mar. 14, 1985, published as WO85/04249 Sept. 26, 1985, now abandoned.

This invention relates to a method of determining size distribution of wood chips. The method can also be used for measurement of other lump material. Chips can, for example, be used for the manufacture of cellulose pulp. The size distribution is determined in respect to volume proportions. If the density of the material is similar for the different large material pieces or if the distribution is known, weight proportions can also be determined from this invention.

The invention is described below in a version specially adapted for measurement of chips for the manufacture of cellulose pulp. However, other materials can also be size determined, for example stones, gravel and sand within the mining, concrete and construction industires and for road building and similar, raw materials and products within agriculture and food industries, etc. The information can be used for determining quality, for production supervision and control of various operations and processes.

The increased demand for good manufacturing economy and high quality during the manufacture of cellulose pulp have increased the need for control of delivered raw materials and for efficient process control systems in order to reduce process disturbances in plants and variations in product quality. Up until now, process disturbances have been met by control processes in the pulp mill, even if they are caused by varying raw material quality. At present, there is an increasing effort to meet variations as early as possible, i.e. in the cleaning department. Production statistics from pulp mills show, for example, that a major part of these disturbances (i.e. production problems and variations in digestions results) in a continuous digester are introduced by the wood raw material.

This has shown the need of a new measurement system for determining chip quality, particularly size distribution of chips. Application fields for such a measuring system include control of choppers, sawmills chips, screening systems and information to the digester operator.

Up until now, the size distribution of chips has been determined using the screening method. A standard method which is often used in Sweden is "STFI's pin chips method". Here the chips are divided into five fractions by means of four screens as follows:

| Screen type | Fractions |
| --- | --- |
| 45 mm round holes | Super-size chips |
| 8 mm slot | Super-thick chips |
| 7 mm round holes | Accept |
| 3 mm round holes | Pin chips |
| | Fine shivers |

In this method the screening apparatus comprises four screen frames. These are placed one above the other and assembled as one unit. The three screen frames with screen plates and round holes separate the chips mainly according to their width and the fourth screen with slots according to their thickness. The unit is pendulum-suspended and can be vibrated via an eccentric rod with a substantially single-dimension horizontal movement.

This method has for a long time been in general use in the cellulose industry, but it is not capable of fulfilling today's demand for a rapid and accurate measuring method in obtaining the measurement values required for process control. Below, the present invention is compared with this method as far as performance is concerned. The "STFI's pins chips method" is used as a reference for method studies. The invention can also be used to determine size distribution according to other norms.

The present invention is based on the problem of achieving a measurment method which eliminates the disadvantages of the conventional screening methods. According to the invention, the problem is solved by using an optical method for determining chip size. To be more specific, the chip material is distributed over a plane conveying surface which advances the material at a pre-determined speed. In the below-described example the speed is constant. At a certain position during feed the material is exposed to light from one or several light sources dependent on each other under optical registration from light reflected from the chips and light reflected from the conveying surface, respectively. The regisration signals are then handled electronically in order to obtain the size distribution.

In the below, the invention is described with an example and with reference to the attached drawings.

Figure 1:
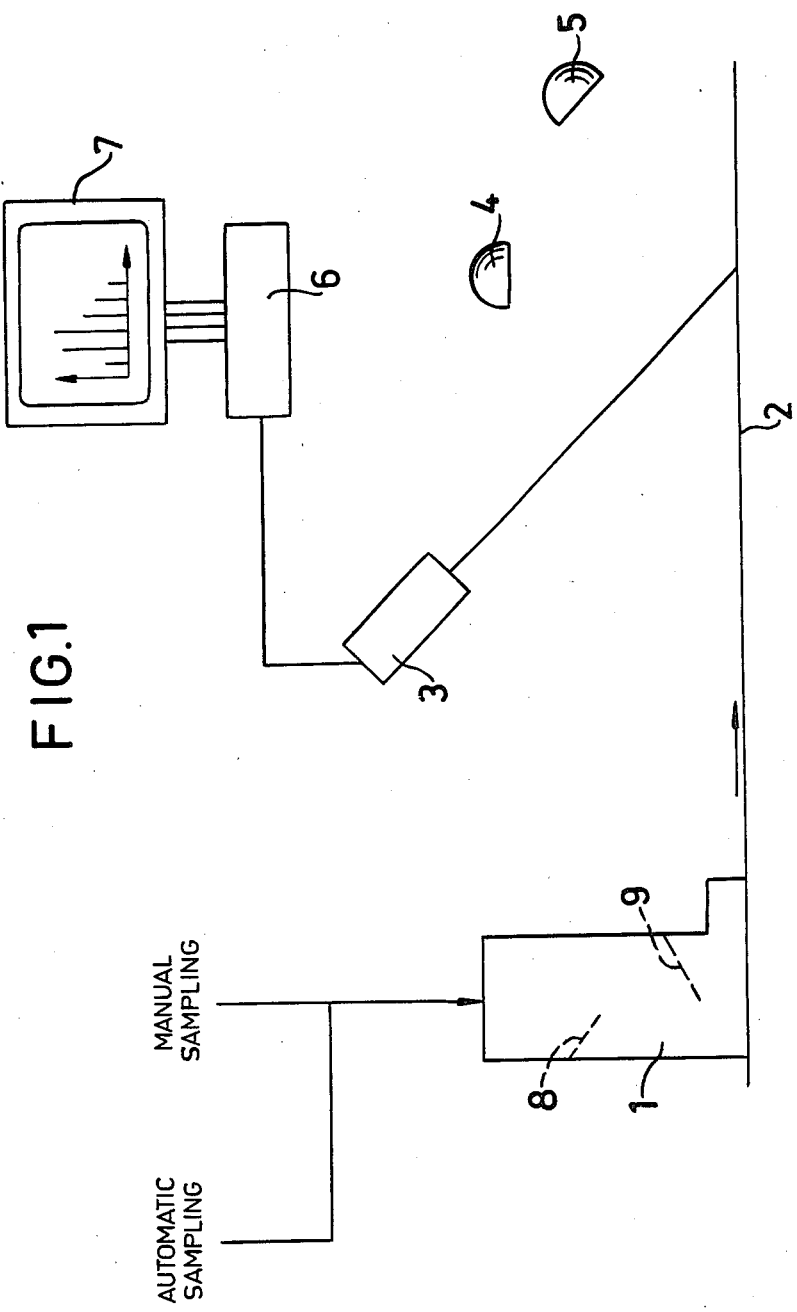
FIG. 1 is a schematic representation of the invention for measuring size distribution of chip material.

FIG. 1 shows schematically an arrangement for measuring the size distribution of wood chips for the manufacture of cellulose pulp. Samples for measurement are taken, either automatically or manually, from the flow of chopped chips (not shown in the figure). The sample material is conveyed to a head box 1, which feeds the chips onto the belt 2 thereby achieving a spread of the material and giving it a measurable form on the belt. This is achieved because the box is equipped with inclined metal sheets or similar devices, the object of which is to distribute the chips evenly over the conveying surface and also separate the sample material and expose it to such force that the slivers attached to the chips are separated from them. This has proved to be extremely important, especially since the chips are moist because the adhesion forces are then high between the chips are slives. Effective separation is necessary since the system must be able to separate the different chip pieces from each other. The chip pieces are spread over the belt. It is important that a particular size fraction is in no way hidden by another. However, when using this method a completely random spreading is not necessary nor is a complete separation of the individual chip pieces from each other.

The chips are thus spread from the head box out on the conveying belt 2 so that the smallest dimension, i.e. thickness, is located perpendicularly to the belt surface. A camera unit 3 is located above the belt, which effects an optoelectric registration of the chips in two dimensions. Here we have chosen a so-called Charge Coupled Device Camera. The unit described here comprises a line scanning camera, interface electronics and voltage supply. By means of the camera a new line of the belt is recorded twice every millisecond. The conveying belt 2 is advanced at a speed of 1 m/s, whereby a resolution of 0.5 mm is achieved. Two halogen lamps 4 and 5 are mounted on separate ramps opposite the belt. The light source 4 is ignited according to a predetermined plan when the surface of the chips is to be measured, and light source 5 is ignited when the thickness of the chips is to be measured. In another version, a number of rows can be recorded with a matrix of TV camera at repeated intervals.

The image from the camera unit 3 is forwarded to a signal processing unit 6 where it is analysed by a specially developed electronic device and in a microcomputer system. In the example the size distribution of the chips is divided into 11 size classes. The information is presented on a viewing screen 7, but can also be forwarded to a process computer. In another version the analysis can be carried out in a dedicated computer system. How the size information is presented and/or further used entirely depends on the individual application.

An installation of the version described above makes it possible to determine a great number of the geometric qualities of the material if the optical resolution is sufficient and electronics and computer power have sufficient processing capacity and suitable software. An example of what can be determined for individual pieces of material and collections are length, width, thickness, area, volume, circumference, diagonal, surface texture etc. There exists today a general image analysis system for determining this information in a laboratory. However, this does not work sufficiently rapidly to be able to determine size distribution for a sufficiently great number of material pieces. It is also more expensive.

The invention is based on a similar technique but by making use of information on the shapes of the material pieces, the relation between their directional properties in various directions and by treating the chips prior to measurement, you can simplify the equipment to that in the example given.

If there exists a correlation between the material pieces' various directional properties, or if one of the directional properties is known, the number of measured dimensions can be reduced. For example, in certain cases, the volume distribution can be calculated based on a measured dimensional distribution for one or two dimensions. A simple example of this is that the volume of a sphere can be calculated from measured diameter or the volume of a flat object with the same thickness can be determined from its surface perpendicular against the direction of the constant thickness. Such correlations exist in the case of chips. The reason is that the wood's tensile properties vary in different directions and due to the way the chips have been produced. The thickness of the chips will therefore correlate with their length. Knowledge of this connection is used in the invention. In this way you achieve a method where the dimensional measurement of a far greater number of chips can be determined. The above-described process also enables the size of the chips to be determined at process time.

Figure 2:
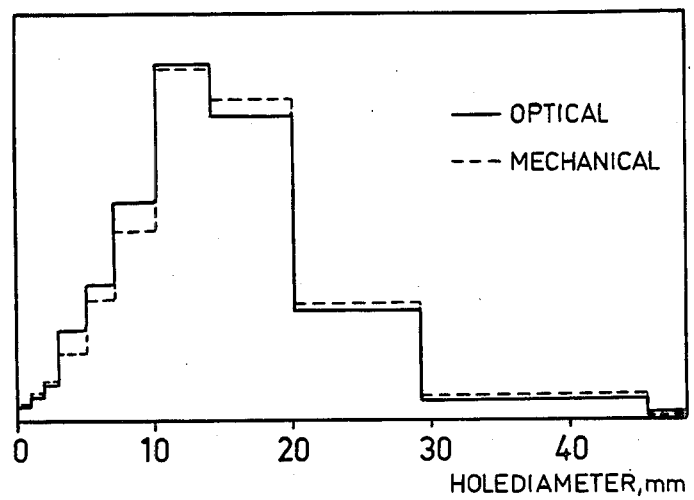
FIG. 2 is a histogram of chip size classes determined by both optical and mechanical methods.

When classifying using "STFI's pin chips method" the chips are classified (i) according to their width (screening through holes) and (ii) according to their thickness (screening through slots). The screening result can be expressed on a volume or weight basis. Given the information from the camera combined with knowledge of the connection between the chip pieces' length, width and thickness, highly detailed information about size distribution can be obtained via electronics and computers. An almost continuous distribution of the size can be obtained. In FIG. 2 the various size proportions have been drawn in a histogram for one and the same chip shipment but determined using both optical and mechanical methods. The size classes are here determined by hole screening.

Figure 3:
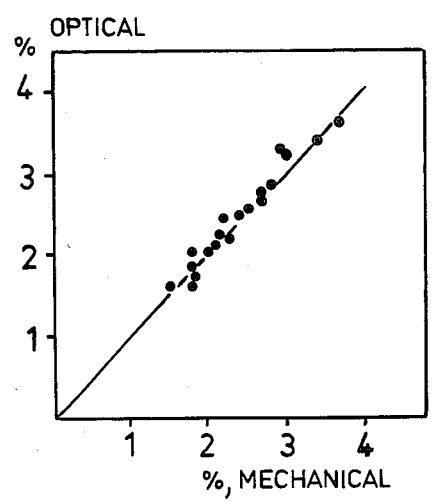
FIG. 3 is a graph of chip thickness screening.

The size classes specified for the "STFI's pin chips method" can also be determined. In order to control this (the method's compatability with mechanical screening) a number of measurement series have been carried out. FIG. 3 shows the measurements made from a thickness screening where the samples are taken in a factory both before and after screening during a 2-day period. The optically determined value for fine slivers is depicted as a function of that from mechanical screening.

Figure 4:
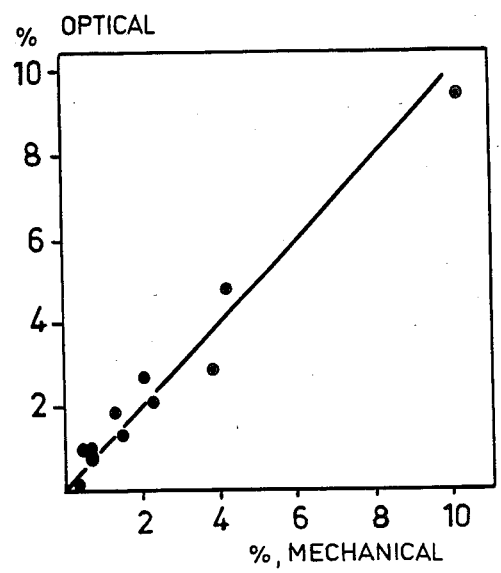
FIG. 4 is a graph similar to FIG. 3 but for a different chip type.

Equivalent comparisons for determining of fine shivers have been made for entirely different chips types, see FIG. 4. The material includes extremes such as chips from adjusting cuts, flawed wood, edging mill chips etc and small different types of wood (birch, spruce, fir) and from various factories.

Figure 5:
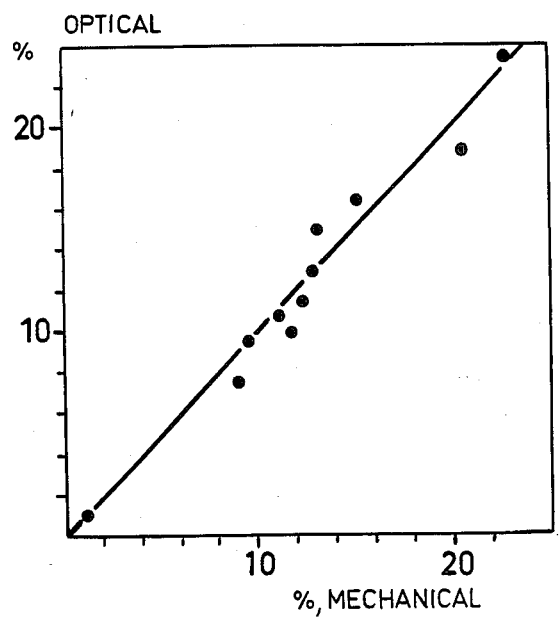
FIG. 5 is a graph similar to FIGS. 3 and 4 but for a further chip type.

For pin chips using the same extreme mixture of different chip types as above a comparative result according to FIG. 5 is obtained. Each point in the diagram implies that the pin chip content has been determined mechanically and optically. FIGS. 2-5 show that these methods have a high correlation.

In addition, the optical method is less sensitive than the mechanical to variations in moisture content and changes in other circumstances which mean that the chips tend to adhere to each other.

When put to practical use, the measurement method according to the present invention has proved to have the following performance:

| Analysis capacity: | 1 m³/h |
| --- | --- |
| Accuracy: | |
| reproductability | |
| fine slivers | ±0.1% |
| pin chips | ±0.5% |
| Agreement with conventional chip screen: | |
| fine slivers | ±0.2% |
| pin chips | ±1.0% |

When comparing the method according to the invention with conventional chip screening, the following can be stated:

The mechanical chip screening determines what has passed through the different hole and slot dimensions after 10 minutes vibration. The result can depend, for example, on the load on different metal sheets and on the moisture content of the chips. The optical method determines what theoretically can pass through different hole or slot dimensions. Determination using the optical method is considerably more independent of moisture content than the mechanical screening method which is powerfully affected by variations in moisture content in the material as a whole and between the different fractions.

The optical method is well suited for on-line measurement.

The invention is not limited to the described example of use but can be varied within the scope of the invention idea.

I claim:

1. A methof for determining the size distribution of wood chip material of varying dimensions for the manufacture of cellulose pulp, including the steps of: distributing the material on a conveying surface so that a substantial majority of the chips are arranged with a shortest dimsnsion of said varying dimensions at substantially right angles to the conveying surface; advancing the conveyor and the materials thereon at a predetermined speed; determining the speed of the conveyor at predetermined times; subjecting the materials to light radiation in the range of 600–800 nanometers provided by at least one light source positioned above the conveying surface, optically registering the materials and obtaining a signal representative of a two dimensional configuration of the material, electronically processing and recording the signal over a number of predetermined two dimensional size classes, using a relation between the chip material width, length and thickness tgether with the processed signals for obtaining the volume of the material pieces, obtaining the size distribution of the chip material on one of a volume and weight basis over the number of predetermined size classes.

* * * * *